United States Patent
Grenier et al.

(10) Patent No.: US 11,915,824 B2
(45) Date of Patent: Feb. 27, 2024

(54) DEVICE FOR MEASURING THE THERAPEUTIC OBSERVANCE OF THE WEARING OF A TEXTILE ITEM BY A PATIENT, INSTRUMENTED ITEM COMPRISING SUCH A DEVICE, AND MEASUREMENT METHOD

(71) Applicant: Sigvaris AG, St. Gallen (CH)

(72) Inventors: Etienne Grenier, Marcilly le Chatel (FR); Cyril Chaigneau, Saint-Etienne (FR)

(73) Assignee: Sigvaris AG, St. Gallen (CH)

( * ) Notice: Subject to any disclaimer, the term of this patent is extended or adjusted under 35 U.S.C. 154(b) by 289 days.

(21) Appl. No.: 17/298,828

(22) PCT Filed: Dec. 9, 2019

(86) PCT No.: PCT/IB2019/060568
§ 371 (c)(1),
(2) Date: Jun. 1, 2021

(87) PCT Pub. No.: WO2020/115724
PCT Pub. Date: Jun. 11, 2020

(65) Prior Publication Data
US 2022/0037010 A1    Feb. 3, 2022

(30) Foreign Application Priority Data
Dec. 5, 2018    (FR) ...................................... 1872335

(51) Int. Cl.
*G16H 40/63*    (2018.01)
*G16H 20/30*    (2018.01)
*G06Q 30/018*   (2023.01)

(52) U.S. Cl.
CPC ........... *G16H 40/63* (2018.01); *G06Q 30/018* (2013.01); *G16H 20/30* (2018.01)

(58) Field of Classification Search
CPC ....... G16H 40/63; G16H 20/30; G06Q 30/018
(Continued)

(56) References Cited

U.S. PATENT DOCUMENTS

| | | |
|---|---|---|
| 2015/0145671 A1 | 5/2015 | Cohen et al. |
| 2017/0181703 A1* | 6/2017 | Kaib ................... A61N 1/3943 |
| 2017/0333256 A1* | 11/2017 | Bassez ................. A61B 5/6807 |

FOREIGN PATENT DOCUMENTS

| | | |
|---|---|---|
| DE | 102008024014 | 4/2010 |
| DE | 102009023228 | 12/2010 |

(Continued)

*Primary Examiner* — Joy Chng
(74) *Attorney, Agent, or Firm* — Forge IP, PLLC

(57) ABSTRACT

A device for measuring therapeutic compliance with wearing a textile item by a patient. The device includes: a flexible electronic card having two opposed faces and designed to be integrated into the item in a manner such that one of the faces is disposed against a limb of the patient when the item is worn; two capacitive electrodes each disposed on one of the faces of the electronic card, orientated in opposing directions and capturing measuring signals which are a function of their environment; a monitoring system disposed on the electronic card and capable of generating compliance data from the measuring signals; and a communications system disposed on the electronic card and designed to transfer data remotely from the item. The device is suitable for selectively detecting Wearing, Not Wearing or Washing of the item, as well as for estimating a potential level of wear of the item.

11 Claims, 3 Drawing Sheets

(58) Field of Classification Search
USPC .......................................................... 705/2–3
See application file for complete search history.

(56) References Cited

FOREIGN PATENT DOCUMENTS

| | | |
|---|---|---|
| FR | 3051354 | 11/2017 |
| WO | WO2014058473 | 4/2014 |

* cited by examiner

| E1 | E2 | E1/E2 | ETAT |
|---|---|---|---|
| C1>S1 | C2>S1 | - | Lavage |
| C1 | C2 | C1-C2>S2 | Porté |
| C1<S1 | C2<S1 | C1-C2<S2 | Non porté |

DEVICE FOR MEASURING THE THERAPEUTIC OBSERVANCE OF THE WEARING OF A TEXTILE ITEM BY A PATIENT, INSTRUMENTED ITEM COMPRISING SUCH A DEVICE, AND MEASUREMENT METHOD

The present invention relates to a device for measuring therapeutic compliance with wearing a textile item by a patient. The invention also relates to an instrumented item comprising a device of this type.

The field of the invention is that of textile items, in particular compression and/or support items such as socks, stockings, tights and cuffs, designed to be worn on the lower or upper limbs of a person.

In order to benefit from an optimized therapeutic effect, it is essential for the wearer of the item to comply with the recommendations of the manufacturer and of the physician. Different systems have therefore been developed in order to evaluate compliance, i.e. observance of the therapeutic treatment.

Some systems comprise tags for pairing items, in order to ensure that the wearer is equipped with a pair of items having characteristics that are adapted to their state of health.

Other systems comprise surface sensors integrated into the items, with a view to detecting when they are worn.

However, in the majority of cases, none of the systems has been integrated into the item and the evaluation of compliance is obtained by a self-assessment questionnaire produced by the patient themselves. The disadvantage with this method, even if it is in the context of organising clinical studies, is that it is associated with a not insubstantial bias in the measurements.

WO 2014/058473 describes an example of a measuring device integrated into a textile item. The device comprises a flexible substrate, a memory, and a sensor that can measure a parameter of a user and/or of their environment. The sensor is impervious, washable, capable of detecting electrical activity and its position/location. The sensor may be constituted by a capacitive sensor and be used to detect perspiration in socks. The data can be transmitted via a NFC antenna formed by a coil.

US 2015/145671 describes another example of a measuring device which has many functions, but is relatively complicated. Preferably, the device comprises a surface sensor with a view to detecting when it is being worn.

The aim of the present invention is to propose a novel solution for managing the use of a compression and/or support item.

To this end, the invention provides a device for measuring therapeutic compliance with wearing a textile item by a patient, the device comprising:
 a flexible electronic card comprising two opposed faces and designed to be integrated into the item in a manner such that one of the faces is orientated towards a limb of the patient when the item is worn;
 two capacitive electrodes each disposed on one of the faces of the electronic card, orientated in opposing directions and capturing measuring signals which are a function of their environment;
 a monitoring system disposed on the electronic card and capable of generating compliance data from the measuring signals; and
 a communications system disposed on the electronic card and designed to transfer data remotely from the item;
the device being suitable for selectively detecting Wearing, Not wearing or Washing of the item, as well as for estimating a potential level of wear of the item.

The device in accordance with the invention may be used to measure three states:
 Washing, if the electrodes each measure a capacity which is larger than a threshold value S1.
 Wearing, if the difference between the capacities measured by the electrodes is larger than a threshold value S2.
 Not wearing, if the capacities measured by the electrodes are lower than the threshold value S1 and that the difference between these capacities is less than the threshold value S2.

Thus, the invention can be used to improve the measurement of therapeutic compliance by the patient using the textile item. By detecting both wearing, not wearing and also washing, the device can be used to monitor compliance by the patient with their treatment, and also compliance with the recommendations for use of the item. In fact, washing can be used to revivify the elastic effect of the textile material yarns, and thus the therapeutic effect of the item.

In accordance with other advantageous characteristics of the invention, taken alone or in combination:
 The electronic card comprises a flexible foil of plastic material and a printed circuit formed on the flexible foil.
 The device comprises an impervious envelope, covering the electronic card and the elements secured to the card, including the capacitive electrodes.
 The envelope is formed from plastic material, in particular silicone.
 The capacitive electrodes have a measurement sensitivity which is a function of their dimensions.
 The capacitive electrodes comprise shielding in order to reduce the sensitivity to electronic noise linked to their environment. The shielding is disposed below the electrode on the other face of the electronic card.
 By way of example, an electrode measures 7 mm in width by 7 mm in height, while the shielding measures 9 mm in width by 13 mm in height.
 The capacitive electrodes are protected by a varnish. The varnish is applied to the electrode, on the corresponding face of the electronic card.
 The monitoring system comprises an accelerometer. The compliance data are generated from the measurements from the capacitive electrodes and from the accelerometer.
 The communications system comprises an RFID or NFC antenna.
 The communications system is specifically adapted to communicate at a frequency of 13.56 MHz.
 The monitoring system and the communications system are configured in a manner such that the transfer of data remotely from the item can be carried out without the use of on board power.
 The monitoring system generates compliance data from measuring signals from the capacitive electrodes, and the compliance data are transferred by the communications system remotely from the device.
 The monitoring system generates digital data from the measuring signals from the capacitive electrodes, the digital data are transferred by the communications system remotely from the device, and the compliance data are generated from digital data exclusively of the device.

The invention also concerns an instrumented item comprising a textile item designed to be worn by a patient, and a device as described above, integrated into the item.

The textile item may be of any type such as socks, stockings, tights or cuffs, designed to be worn on the lower or upper limb of a person.

Preferably, the textile item is a compression and/or support item.

The device may be integrated into the textile item by any means that can guarantee its positioning and function.

The device may be inserted between the two textile walls of the item, for example the turn-up of a sock.

The device may be housed in a flexible, thin pouch which may be integrated into the item by bonding, heat bonding and/or stitching.

The invention also pertains to a method for measuring therapeutic compliance with wearing a textile item by a patient, using a device as mentioned above. The method comprises the following steps:
a) a measuring step, in which the two capacitive electrodes orientated in opposing directions capture measuring signals which are a function of their environment;
b) a signal processing step, in which digital data are generated from the measuring signals from the capacitive electrodes;
c) a transfer step, in which data are transferred from the device remotely from the item, these data comprising the compliance data and/or the digital data which can be used for determining the compliance data;
d) a digital data processing step, in order to generate compliance data, either in the device before the transfer step, or remotely from the device after the transfer step.

BRIEF DESCRIPTION OF THE DRAWINGS

The invention will be better understood from the following description which is given solely by way of non-limiting example and is made with reference to the accompanying drawings, in which.

DETAILED DESCRIPTION OF THE INVENTION

Figure 1:
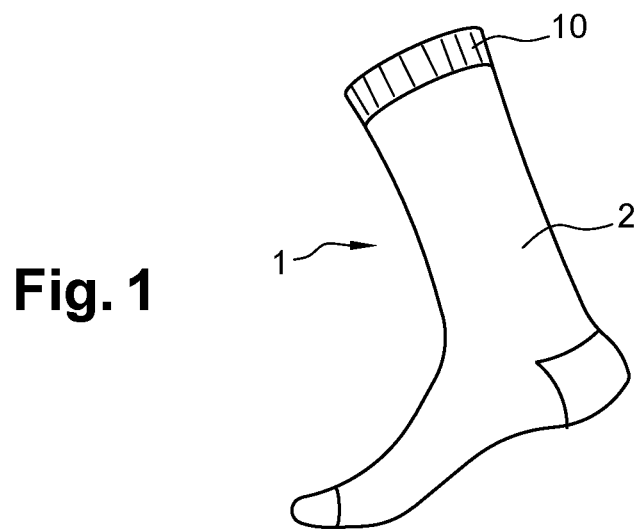
FIG. 1 is a side view of an instrumented item in accordance with the invention, comprising a textile item of the sock type designed to be worn by a patient, and a device for measuring therapeutic compliance integrated into the item.
Figure 2:
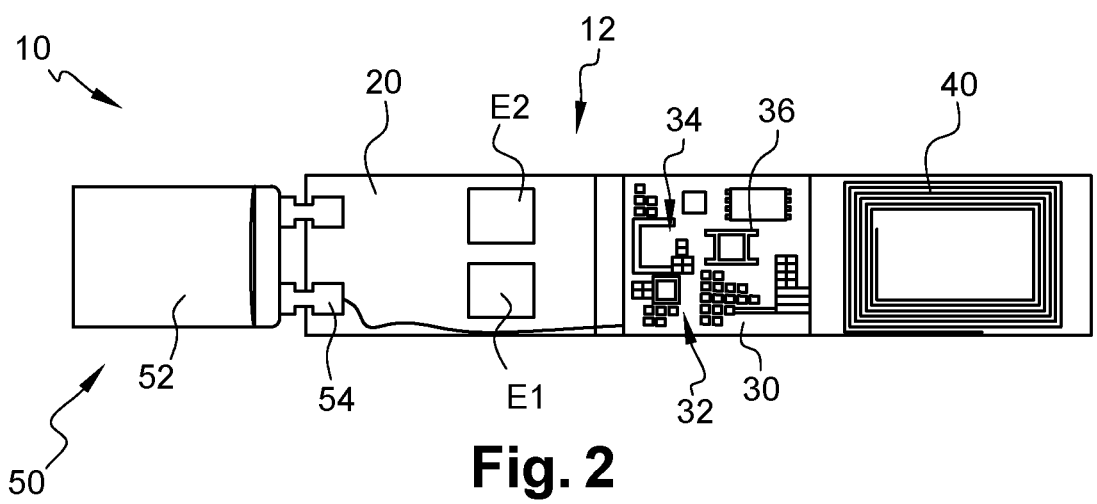
FIG. 2 is a front view of the device in accordance with the invention.
Figure 3:
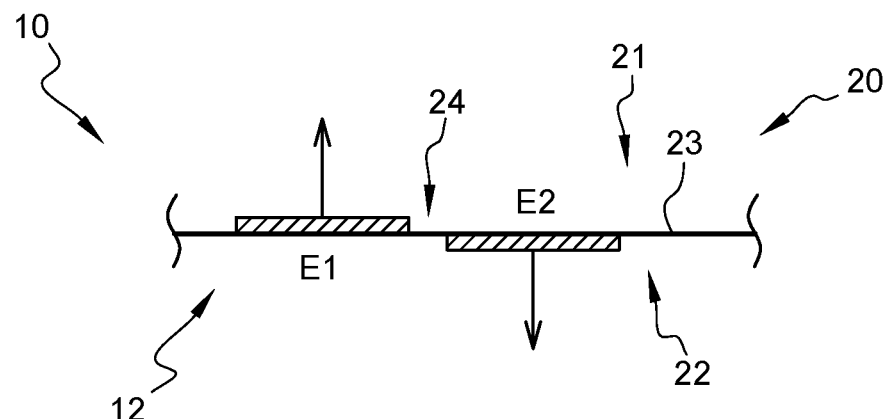
FIG. 3 is a partial view from above of the device in accordance with the invention.

FIGS. 1 to 3 show a device (10) in accordance with the invention, provided on a textile item (2) of the support sock type. The device (10) is designed to measure therapeutic compliance with wearing of the item (2) by a patient.

The device (10) comprises an electronic card (20), two capacitive electrodes (E1, E2), a monitoring system (30), a communications system (40) and a power supply system (50).

The device (10) comprises an impervious envelope (12), entirely covering the electronic card (20) and the elements (E1, E2, 30, 40, 50) secured to the card (20), including the capacitive electrodes (E1, E2). The envelope (12) is preferably produced from plastic material, for example silicone. The envelope (12) may be transparent, translucent or opaque.

The electronic card (20) is thin and comprises two opposing faces (21, 22), including an inner face (21) and an outer face (22). The electronic card (20) is flexible, so that it can be wrapped around a limb of the patient. The electronic card (20) is designed to be integrated into the item (2) in a manner such that the inner face (21) is orientated towards a limb of the patient wearing the item (2). In practice, the contact between the device (10) and the skin of the patient is not direct because the thickness of the textile and the thickness of the impervious envelope (12) lie between the skin and the face (21).

The electronic card (20) comprises a flexible foil (23) of plastic material and a printed circuit (24) formed on the flexible foil (23).

The two capacitive electrodes (E1, E2) constitute compliance sensors. The electrodes (E1, E2) are designed in order to measure a capacity (C) which varies as a function of the environment. In particular, the capacity (C) varies as a function of the proximity to skin, water or air.

Figure 6:
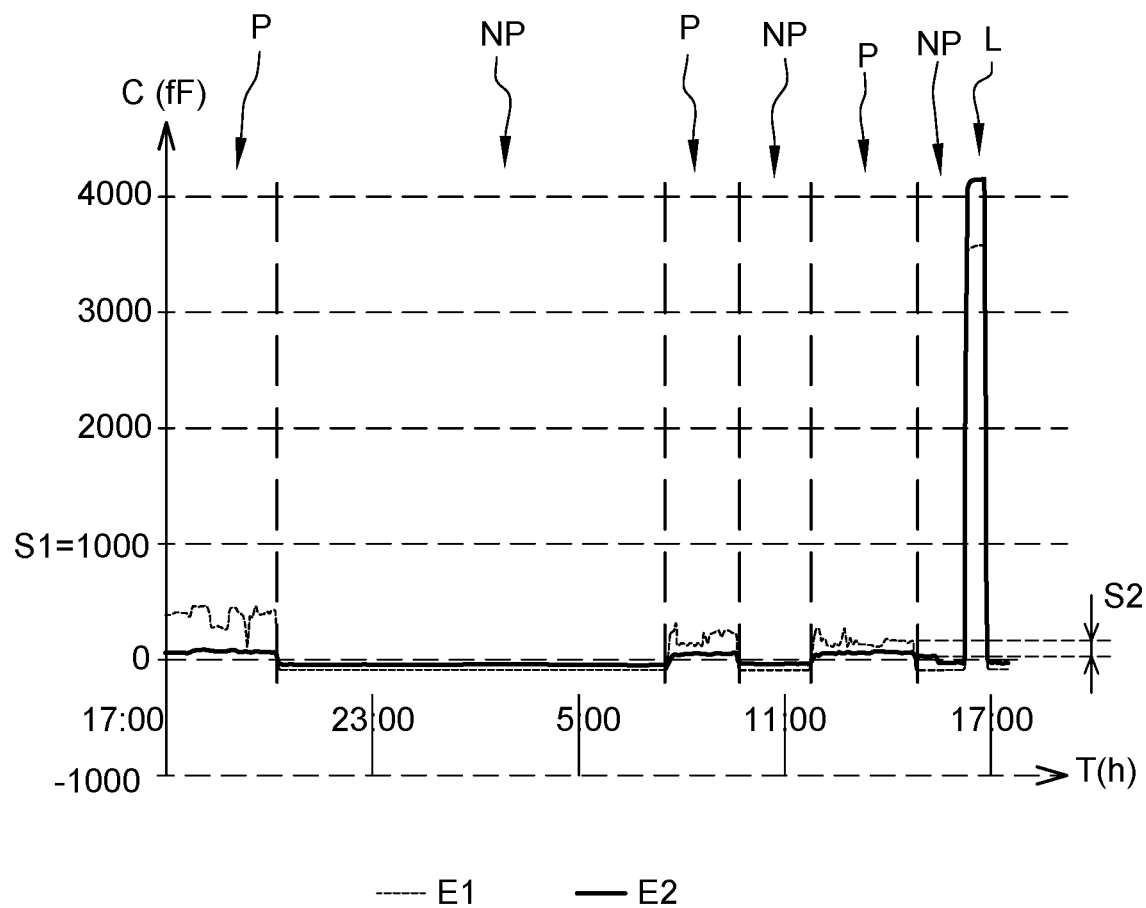
FIG. 6 is a graph illustrating an experiment showing the various states which can be measured by the device.

As can be seen in FIG. 6, the capacity (C) is high when the electrode (E1, E2) is in the proximity of the skin, very high in the proximity of water, and very low in the proximity of air. The compliance measurements may be carried out directly in contact with the skin, or through a small thickness of fabric.

The electrodes (E1, E2) may be produced from copper and formed directly on the printed circuit (24). The electrodes (E1, E2) are each disposed on one of the faces (21, 22) of the electronic card (20) and orientated in opposing directions. Thus, only one of the electrodes (E1, E2) may be directed towards the limb of the patient wearing the item (2). An inner electrode (E1) is disposed on the inner face (21) and an outer electrode (E2) is disposed on the outer face (22).

When the inner face (21) of the device (10) is orientated towards a limb of the patient wearing the item (2), the inner electrode (E1) is positioned against the skin or in the proximity of the skin of the patient.

The monitoring system (30) comprises several components (32, 34, 36) disposed on the printed circuit (24) of the card (20).

The system (30) comprises a microprocessor (32) configured to process the signals deriving from the electrodes (E1, E2). More precisely, the microprocessor (32) can be used to periodically convert the analogue signals obtained from the capacitive electrodes (E1, E2) into digital data or digitized signals. In addition, the microprocessor (32) can convert the digital data or digitized signals into compliance data (P/NP/L).

The system (30) comprises a memory (34) configured to record digital data after processing by the microprocessor (32).

The microprocessor (32) can generate the compliance data (P/NP/L) from the signals obtained from the electrodes (E1, E2), then store them in the memory (34). As an alternative, the microprocessor (32) may generate digital data which will be processed after transfer remotely from the device (10), in order to generate the compliance data (P/NP/L). Different functional modes of the device (30) are detailed below.

Processing of signals by the microprocessor (32) as well as the transfer and recording of data in the memory (34), means that energy from the onboard power supply system (50) is consumed by the device (10).

Preferably, the monitoring system (30) comprises an accelerometer (36). Thus, the compliance data (P/NP/L) can be generated from measurements from the capacitive electrodes (E1, E2) and from the accelerometer (36).

As an alternative, the compliance data (P/NP/L) may be generated solely from capacitive measurements (C) from the capacitive electrodes (E1, E2).

The communications system (40) is disposed on the electronic card (20) and designed for the transfer of data generated by the monitoring system (30).

The transfer of data is bidirectional: importing for the configuration of the device (10) and exporting for the recovery of data by remote equipment.

The transfer of data is carried out by radiofrequency communication with a reader/encoder, a computer, a smartphone, or any other system.

Preferably, the communications system (40) comprises an antenna which is compatible with NFC and/or RFID technologies. The NFC communication distance between the antenna and a NFC reader is of the order of a few centimetres. The RFID communication distance between the antenna and an RFID reader is of the order of a metre.

Preferably again, the system (50) communicates at the frequency 13.58 MHz. RFID technology uses several frequency bands, including the frequency 13.58 MHz. NFC technology is based on the frequency 13.58 MHz.

The power supply system (50) comprises a battery (52) and connectors (54), meaning that the battery (52) can be connected to the card (20). The connectors (54) are, for example, studs soldered onto the card (20). The system (50) can be used to supply the system (30) with power.

Advantageously, the memory (34) and the communications system (40) do not use the onboard energy when reading data via remote equipment, such as a smartphone. In fact, the power necessary for operating the communications is supplied by the equipment (reader/encoder), and not by the system (50). This power may be supplied by the electromagnetic fields emitted by the equipment.

The device (10) is adapted for determining compliance data (P/NP/L), i.e. selectively detecting wearing (P), not wearing (NP) or washing (L) of the item (2). The device (10) can be used to evaluate durations of wearing (P) or not wearing (NP), as well as the number and the frequency of washes (L) of the item (2).

In a complementary manner, the device (10) can thus be used to evaluate the probable level of wear of the item (2), linked to a duration in use which is longer than the optimal duration guaranteed by the manufacturer, in particular in the case in which wearing data (P) are also recorded after this optimal duration. Similarly, regular washing (L) forms part of the recommendations for use of the item (2), because the mechanical action which is caused can be used to restore the initial geometric characteristics of the textile structure. In addition to the hygiene aspect, a restricted number of washes (L) compared with the wearing time (P) could indicate a lower therapeutic effectiveness than that normally envisaged by the manufacturer and written down in the conditions for use of the item (2).

As a function of its configuration, the device (10) may function in accordance with one of the three modes discussed below.

Hereinbelow, a "slot" is defined as a set of data recorded at a time t.

First functional mode (normal mode):
a) Capacitive electrodes (E1, E2) capture analogue signals.
b) Microprocessor (32) transforms analogue signals into digital data.
c) Microprocessor (32) processes digital data in order to generate compliance data (P/NP/L).
d) Memory (34) records a set of compliance data (P/NP/L), without recording the digital data used to determine the compliance data (P/NP/L).
e) Antenna (40) transmits compliance data (P/NP/L) recorded in the memory (34) to equipment which is separate from the device (10) via a wireless link.

In this first mode, in each slot, only the compliance datum (wearing/not wearing/washing information) is recorded in the memory (34). This mode is relatively economical as regards power and can be used to store a large number of slots. In contrast, it cannot be used to gain access to physical data which are used to determine the compliance data.

Second functional mode (log mode):
a) Capacitive electrodes (E1, E2) capture analogue signals.
b) Microprocessor (32) transforms analogue signals into digital data.
c) Microprocessor (32) processes digital data in order to generate compliance data (P/NP/L).
d) Memory (34) records a set of digital data and compliance data (P/NP/L).
e) Antenna (40) transmits digital data and compliance data (P/NP/L) recorded in the memory (34) to a device which is separate from the device (10) via a wireless link.

This second mode uses more memory, but improves traceability, compared with the aforementioned mode.

By way of example, for a given configuration of the device (10), the first mode can be used to record up to 32704 slots, while the second mode can be used to record up to 1022 slots.

Third functional mode:
a) Capacitive electrodes (E1, E2) capture analogue signals.
b) Microprocessor (32) transforms analogue signals into digital data.
c) Memory (34) records a set of digital data.
d) Antenna (40) transmits digital data recorded in the memory (34) to a device which is separate from the device (10) via a wireless link.
e) Device processes digital data in order to generate compliance data (P/N P/L)

This third mode provides a compromise between the first and second modes as regards the use of the memory (34) and of the battery (52). The generation of compliance data (P/NP/L) is external to the device (10).

Figures 4, 5:
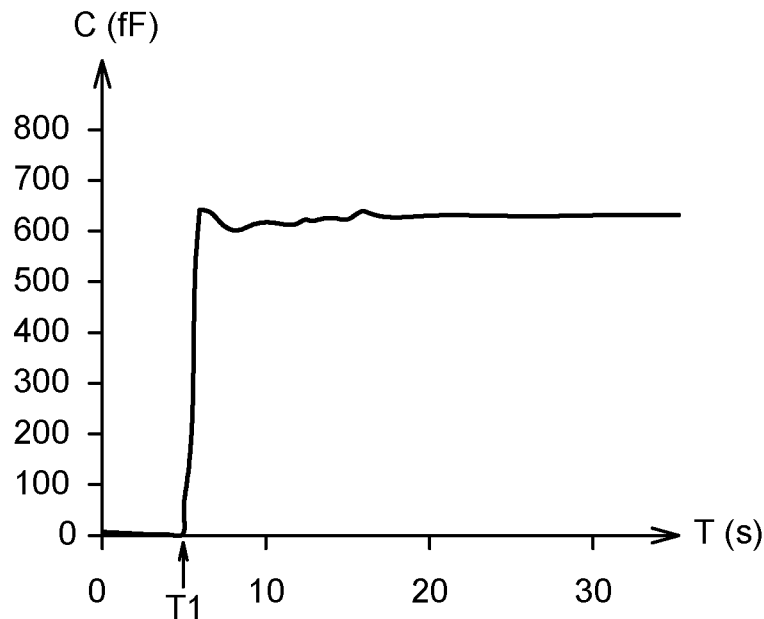
FIG. 4 is a graph illustrating a capacitive measurement carried out by an electrode.
FIG. 5 is a table illustrating the various states which can be measured by the device.

FIG. 4 is a graph showing measurements for the capacity (C) carried out by one of the electrodes (E1, E2). The time (T) in seconds (s) is shown along the abscissa, while the capacity (C) in femtofarads (fF) is shown up the ordinate. The capacity (C) represents the quantity of electric charge carried by a conductive element for a given electrical potential.

On the graph, the capacity (C) increases at a time (T1) corresponding to about 5 seconds when the electrode is brought into contact with a limb of a patient.

Skin and water have capacitive properties which are very different from those of air. The capacity (C) obtained from each electrode (E1, E2) varies as a function of contact or proximity to skin or water.

FIG. 5 is a table showing the different states which can be measured by the device (10):

Washing (L), if the two electrodes (E1, E2) each measure a capacity (C) larger than a threshold value (S1). This threshold value (S1) can be customized and supplied to the system (30) during configuration thereof. The capacity (C) measured by the outer electrode (E2) is generally larger than the capacity (C) measured by the inner electrode (E1). As a complement to this, the accelerometer (36) can be used to detect the particular movements of the item (2) in a washing machine.

Wearing (P), if the difference between the capacities (C) measured by the two electrodes (E1, E2) is greater than a threshold value (S2). This threshold value (S2) can be customized and supplied to the system (30) during configuration thereof. The capacity (C) measured by the inner electrode (E1) is larger than the capacity (C) measured by the outer electrode (E2). As a complement to this, the accelerometer (36) can be used to detect a patient's movements.

Not wearing (NP), if the capacities (C) measured by the two electrodes (E1, E2) are less than the threshold value (S1) and the difference between these capacities (C) is less than the threshold value (S2). As a complement to this, the accelerometer (36) can be used to detect the motionless state of the item (2).

FIG. 6 represents a graph similar to that of FIG. 6, showing the measurements for the capacity (C) carried out by the two electrodes (E1, E2). The time (T) in hours (h) is shown along the abscissa, while the capacity (C) in femtofarads (fF) is shown up the ordinate.

The graph shows a succession of wearing (P) and not wearing (NP) states, then washing (L) of the item (2). When being worn (P), the greater distance above the threshold value (S2) between the measurements for the capacity (C) from the two electrodes (E1, E2) should be noted. When not being worn (NP), the similarity between the measurements for the capacity (C) from the two electrodes (E1, E2), at a calibration value of close to zero should be noted. When being washed (L), the very high measurements for the capacity (C) from the two electrodes (E1, E2), well above the threshold value (S1), should be noted.

If a state changes over a short period, its value is replaced by the next state (averaging states over time). This is the case, for example, when the item (2) is being worn (P), and the difference between the capacities (C) measured by the two electrodes (E1, E2) briefly drops below the threshold value (S2).

The conformation of the item (2) and the device (10) may differ from that of FIGS. 1 to 3 without departing from the scope of the invention defined in the claims. Furthermore, the technical features of the various embodiments and variations mentioned above may be combined in their entirety or only in part. Thus, the device (10) can be adapted in terms of cost, functions and performance.

The invention claimed is:

1. A device for measuring therapeutic compliance with wearing a textile item by a patient, the device comprising:
   a flexible electronic card comprising two opposed faces and designed to be integrated into the item in a manner such that one of the faces is orientated towards a limb of the patient when the item is worn;
   two capacitive electrodes each disposed on one of the faces of the electronic card, orientated in opposing directions and capturing measuring signals which are a function of their environment;
   a monitoring system disposed on the electronic card and capable of generating compliance data from the measuring signals; and
   a communications system disposed on the electronic card and designed to transfer data remotely from the item;
   the device being suitable for selectively detecting Wearing, Not Wearing or Washing of the item, as well as for estimating a potential level of wear of the item.

2. The device as claimed in claim 1, characterized in that the electronic card comprises a flexible foil of plastic material and a printed circuit formed on the flexible foil.

3. The device as claimed in claim 1, characterized in that the device comprises an impervious envelope.

4. The device as claimed in claim 1, characterized in that the monitoring system comprises an accelerometer and in that the compliance data are generated from measurements from the capacitive electrodes and from the accelerometer.

5. The device as claimed in claim 1, characterized in that the monitoring system and the communications system are configured in a manner such that the transfer of data remotely from the item can be carried out without the use of onboard energy.

6. The device as claimed in claim 1, characterized in that the monitoring system generates compliance data from the measuring signals from the capacitive electrodes, and the compliance data are transferred by the communications system remotely from the device.

7. The device as claimed in claim 1, characterized in that the monitoring system generates digital data from the measuring signals from the capacitive electrodes, the digital data are transferred by the communications system remotely from the device, and the compliance data are generated from digital data exclusively of the device.

8. The device as claimed in claim 1, wherein the two capacitive electrodes comprise a first electrode on one of the faces of the card for measuring a first capacity, and a second electrode on the other face of the card for measuring a second capacity, wherein the detection of Wearing and Not Wearing is based on whether the difference between the first capacity and the second capacity exceeds a threshold.

9. An instrumented item comprising a textile item designed to be worn by a patient, and a device as claimed in claim 1, integrated into the item.

10. The instrumented item as claimed in claim 9, characterized in that the item is a compression and/or support item.

11. A method for measuring therapeutic compliance with wearing a textile item by a patient, the method comprising:
   a) providing a flexible electronic card comprising two opposed faces and designed to be integrated into the item in a manner such that one of the faces is orientated towards a limb of the patient when the item is worn, the electronic card having two capacitive electrodes each disposed on one of the faces of the electronic card and orientated in opposing directions, a monitoring system capable of generating compliance data, and a communications system designed to transfer data remotely from the item;
   b) capturing measuring signals with the two capacitive electrodes orientated in opposing directions, which signals are a function of their environment;
   c) generating digital data from the measuring signals from the capacitive electrodes;
   d) transferring data from the device remotely from the item;
   e) processing the digital data to generate the compliance data, either with the device before the data is transferred, or remotely from the device after the data is transferred.

* * * * *